United States Patent [19]
Lee

[11] Patent Number: 5,855,604
[45] Date of Patent: *Jan. 5, 1999

[54] METHOD AND APPARATUS FOR ADJUSTING CORNEAL CURVATURE USING A SOLID FILLED CORNEAL RING

[75] Inventor: Joseph Lee, Loma Linda, Calif.

[73] Assignee: MicroOptix, LLC, Loma Linda, Calif.

[ * ] Notice: The term of this patent shall not extend beyond the expiration date of Pat. No. 5,733,334.

[21] Appl. No.: 829,846

[22] Filed: Apr. 1, 1997

Related U.S. Application Data

[63] Continuation-in-part of Ser. No. 761,362, Dec. 9, 1996.

[51] Int. Cl.⁶ .................................. A61F 2/14; A61F 9/00
[52] U.S. Cl. ................................ 623/5; 606/166; 606/167
[58] Field of Search ............................. 623/4.5; 606/107, 606/166, 167

[56] References Cited

U.S. PATENT DOCUMENTS

| | | |
|---|---|---|
| 4,298,004 | 11/1981 | Schachar et al. . |
| 4,452,235 | 6/1984 | Reynolds . |
| 4,607,617 | 8/1986 | Choyce . |
| 4,624,669 | 11/1986 | Grendahl ...................................... 623/5 |
| 4,655,774 | 4/1987 | Choyce ........................................ 623/5 |
| 4,688,570 | 8/1987 | Kramer et al. . |
| 4,815,463 | 3/1989 | Hanna . |
| 4,834,750 | 5/1989 | Gupta ........................................... 623/6 |
| 4,941,093 | 7/1990 | Marshall et al. .................... 364/413.01 |
| 4,961,744 | 10/1990 | Kilmer et al. ............................ 606/166 |
| 4,976,719 | 12/1990 | Siepser ..................................... 606/151 |
| 5,090,955 | 2/1992 | Simon ........................................ 604/51 |
| 5,123,921 | 6/1992 | Werblin et al. .............................. 623/5 |
| 5,188,125 | 2/1993 | Kilmer et al. ............................ 128/898 |
| 5,236,970 | 8/1993 | Christ et al. ............................... 523/113 |
| 5,300,118 | 4/1994 | Silvestrini et al. .......................... 623/5 |
| 5,312,424 | 5/1994 | Kilmer et al. ............................ 606/151 |
| 5,318,047 | 6/1994 | Davenport et al. ...................... 128/898 |
| 5,331,073 | 7/1994 | Weinschenk, III et al. ............. 526/264 |
| 5,391,201 | 2/1995 | Barrett et al. ............................... 623/5 |
| 5,405,384 | 4/1995 | Silvestrini ................................... 623/5 |
| 5,466,260 | 11/1995 | Silvestrini et al. .......................... 623/5 |
| 5,480,950 | 1/1996 | Wang et al. ............................. 526/258 |
| 5,505,722 | 4/1996 | Kilmer et al. ............................... 601/1 |
| 5,547,468 | 8/1996 | Simon et al. ............................. 604/21 |

FOREIGN PATENT DOCUMENTS

| | | |
|---|---|---|
| 388746 | 7/1973 | Russian Federation . |
| 2 095 119 | 9/1982 | United Kingdom ....................... 623/5 |
| 95/03755 | 2/1995 | WIPO ....................................... 623/5 |

OTHER PUBLICATIONS

"Refractive Surgery," by Dimitri T. Azar, M.D., pp. 1–2, *Corneal Biomechanics in Refractive Surgery*, by Jesper O. Hjortdal, Chap. 15, pp. 197–208, *The Intrastromal Corneal Ring for the Correction of Myopia*, by Steven M. Verify & David J. Schanzlin, Chap. 27, pp. 365–372, *Intracorneal Alloplastic Inclusions*, by Johnny M. Khoury, et al., Chap. 28, pp. 373–384, Appleton & Lange, Stamford, Connecticut. Copyright 1997.

(List continued on next page.)

*Primary Examiner*—Mary Beth Jones
*Attorney, Agent, or Firm*—McCutchen, Doyle, Brown & Enersen, LLP

[57] ABSTRACT

A method and apparatus for adjusting corneal curvature of the eye comprising an adjustable split device formed of a flexible hollow shell which is implantable into the cornea in encircling relation to the central optic zone of the cornea. The implant is filled by a predetermined amount with a select quantity of solid biocompatible material in various forms such as rings or strands and composed of flexible polymeric materials of various shape and length. The biocompatible filler material is strategically located within the flexible shell to alter its dimensions in thickness or diameter and thereby adjust the corneal curvature to correct for refractive error. Further adjustment of the implant may be made post-operatively after implantation by select removal of the biocompatible filler material, shifting of the material, or addition of new material to the device.

32 Claims, 12 Drawing Sheets

OTHER PUBLICATIONS

"*Principles and Practice of Refractive Surgery*," by Richard Elander, M.D., et al., pp. 1–3, *Alloplastic Materials in Lamellar Surgery*, by Bernard E. McCarey, pp. 261–276, *Synthetic Epikeratoplasty*, by Keith P. Thompson, et al., Chap. 39, pp. 405–413, *Intrastromal Corneal Ring*, by David J. Schanzlin, et al., Chap. 40, pp. 415–419, W. B. Saunders Company, Philadelphia, Pennsylvania. Copyright 1997.

Abstract entitled: "*Results of a 2–year animal experiment with reticulated polyethylene oxide intrastromal rings*," by F. Kuhne, et al., Journal of Fr. Ophthalmology, vol. 17, 1994.2.

Abstract entitled: "*Refractive Modeling of the Corneal by Intrastromal Rings*," by Gabriel Simon, et al., Association of Research in Vision and Ophthalmology, Annula Spring Meeting, Sarasota, Forida, Apr. 30–May 5, 1989, p. 187.

"*Effects of Intrastromal Corneal Ring Size and Thickness on Corneal Flattening in Human Eye*," by Terry E. Burris, et al., Refractive & Corneal Surgery, vol. 7 Jan./Feb. 1991, pp. 46–50.

"*Hydration Stability of Intracorneal Hydrogel Implants*," by W. Houdijin Beekhuis, et al., Investigative Ophthalmology & Visual Science/Nov. 1985, vol. 26, pp. 1634–1636.

"*Complications of Hydrogel Intracorneal Lenses in Monkeys*," by W. Houdijin Beekhuis, MD, et al. Arch Ophthalmol, vol. 105, Jan. 1987, pp. 116–122.

"*Hydrogel keratophakia: a microkeratome dissection in the monkey model*," by W. Houdijn Beekhuis, et al., British Journal of Ophthalmology, 1986, 70, 192–198.

"*The Intrastromal Corneal Ring: Two Cases in Rabbits*," by Joseph, F. Fleming, MD., et al., Journal of Refractive Surgery, Nov./Dec. 1987; vol. 3, No. 6, pp. 227–232.

"*Effect of Diameter and Depth on the Response to Solid Polysulfone Intracorneal Lenses in Cats*," by Harold Climenhaga MD., et al., Arch Ophthalmol, vol. 106, Jun. 1988, pp. 818–824.

"*Flattening of central corneal curvature with Intrastromal Corneal Rings of increasing thickness: An eye–bank eye study*," by Terry E. Burris, et al., J. Cataract Refractive Surgery, vol. 19, Supplement 1993, pp. 182–187.

"*Refractive Keratoplasty in Monkeys Using Intracorneal Lenses of Various Refractive Lenses*," by Bernard E. McCarey, PhD, et al., Arch Ophthalmol, vol. 105, Jan. 1987, pp. 123–126.

*Refractive keratoplasty with intrastromal hydrogel lenticular implants*, by Bernard E. McCarey, et al., Investigative Ophthalmology Visual Science, Jul. 1981, vol. 21, No.1, Part 1, pp. 107–115. Copyright 1981.

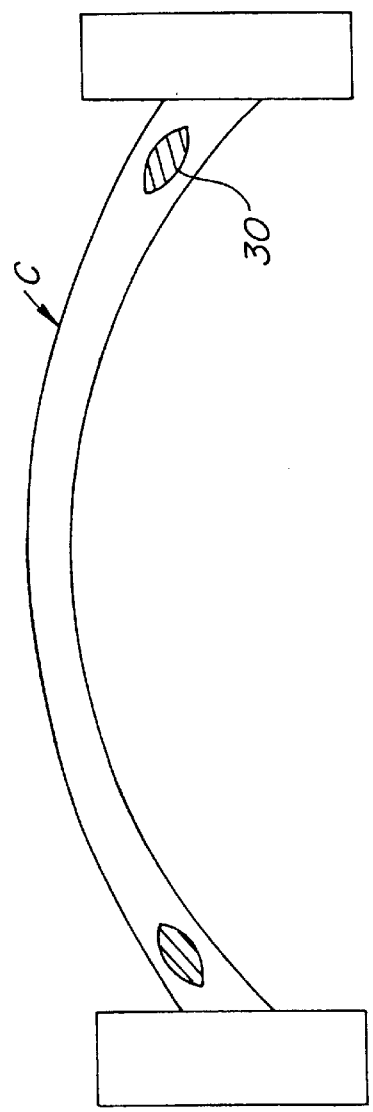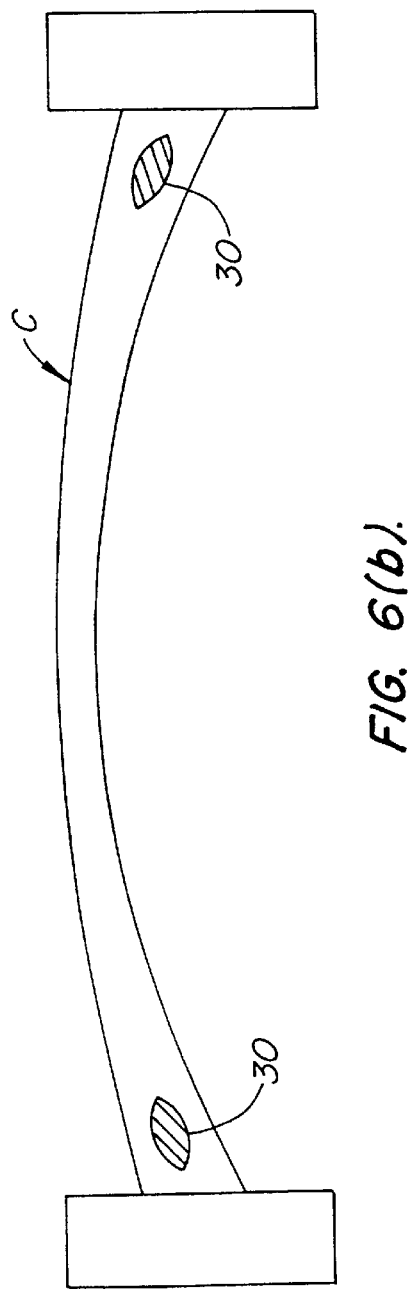
FIG. 6(a).
FIG. 6(b).

METHOD AND APPARATUS FOR ADJUSTING CORNEAL CURVATURE USING A SOLID FILLED CORNEAL RING

CROSS-REFERENCE TO RELATED APPLICATIONS

This application is a continuation-in-part of U.S. patent application Ser. No. 08/761,362, filed Dec. 9, 1996.

BACKGROUND OF THE INVENTION

This invention relates to a method and apparatus for adjusting corneal curvature and, more particularly, to an implantable device adapted for insertion into the cornea of an eye and which may be modified in the amount of volume it displaces at the time of insertion and at post-operative times to correct refractive error by adjusting or removing solid material from the implanted device or augmenting said device with solid material.

Ametropia, an undesirable refractive condition of the eye, has three main subdivisions: myopia, hyperopia, and astigmatism. In myopia, by far the most common type of ametropia, the parallel light rays 20 which enter the eye as shown in FIG. 1 come to a focus F1 in front of the retina 24 as shown in FIG. 2. In hyperopia, the rays of light 20 come to a focus F2 behind the retina 24 as shown in FIG. 2 When the rays of light converge to not one, but several foci, it is referred to as astigmatism, in which condition the various foci may all lie before the retina; all lie behind the retina; or partly before and partly behind the retina.

Ametropia is usually corrected by glasses or contact lenses. However, these refractive disorders may also be corrected by surgery. Refractive eye surgery is defined as that surgery on the eye which acts to change the light-bending qualities of the eye. More common current refractive procedures include radial keratotomy, as described in U.S. Pat. Nos. 4,815,463 and 4,688,570 and also laser ablation of corneal stroma, described in U.S. Pat. No. 4,941,093. Various other surgical methods for the correction of refractive disorders have been tried including thermokeratoplasty for the treatment of hyperopia, epikeratoplasty to correct severe hyperopia, and keratomileusis which can steepen or flatten the central cornea. Keratomileusis was introduced by Barraquer of Colombia in 1961 and essentially involves grinding a corneal button into an appropriate shape to correct the refractive error and replacing the reshaped corneal button. Some of the more common keratorefractive procedures are discussed below, none of which have currently shown itself to have all the characteristics of an ideal keratorefractive procedure. The disadvantages of corneal refractive surgery include limited predictability, lack of reversibility, corneal destabilization, optical zone fibrosis, post-operative discomfort, and visual symptoms such as glare, halos, and starbursts.

In radial keratotomy (RK) multiple peripheral radially directed incisions are made into the cornea at 90–95% depth in an attempt to flatten the central cornea and thus correct myopia. The problem of unpredictability of result was tackled by multiple extensive retrospective analyses of the patients in whom surgery had already been performed. These studies revealed certain factors that seemed to control the outcome of the surgery, such as the size of the optical zone, the initial keratometric readings, corneal diameter, corneal rigidity, number of incisions, incision depth, intraocular pressure, thickness of the cornea, and degree of astigmatism. Age and sex are also factors that are taken into consideration in most of the nomograms which have been devised to predict what effect to expect for a certain surgery. At one point, many experts in the field considered it nearly impossible to fully and accurately correct patients in one surgery and felt that RK should be considered a two-stage surgery, with the initial surgery to achieve the "ball-park" correction, followed by an enhancement procedure to adjust or titrate the result near the desired outcome for an individual eye. It was felt that because of individual variability which may lead to an under or over-correction in the individual different from that predicted by the nomogram, attempting to fully correct the refractive error in one surgery could lead to over-correction in a not insignificant percent of the surgeries, resulting in hyperopia which is much more difficult to correct. Unfortunately, the second-stage surgery is even less predictable than the initial procedure. No one has yet devised a formula to take into account the profound changes which occur in the cornea after the initial RK, especially when weeks or months have passed. Most studies quote only 50–60% of eyes achieving 20/20 or better visual acuity following RK. Patients who are accustomed to 20/20 or better corrected visual acuity before surgery are not typically satisfied with less than 20/25 or 20/30 uncorrected post-operative visual acuity.

In addition, a gradual hyperopic shift is a major concern after RK. Refractive stability is critical for all refractive procedures but all corneal refractive procedures show significant degrees of instability. To date, there have been no clear explanation of why the cornea is destabilized by RK. A recent report on the long-term results of RK stressed the "natural" hyperopic refractive progression of "normal" eyes as a function of age. It is possible that patients are initially over corrected and the over-correction masked by the patient's accommodative powers. With time and loss of accommodation, the hyperopia may be gradually unmasked with the hyperopia becoming visually symptomatic. At the time of surgery, a patient may be corrected with resultant slight hyperopia and yet have 20/20 vision because of the ability of the lens to accommodate. There is a range of residual correction within which the patient can have 20/20 ncorrected vision. This range varies depending on the individual but probably spans two to three diopters. Even with this range, the percentage achieving 20/20 is only 50–60%. This reflects poorly on the precision of the technique. It is important to note that this range diminishes with presbyopia, or loss of accommodation which usually begins at about 45 years of age. This results in the percentage achieving 20/20 dropping from the 50–60% described above. It is obvious that RK does not qualify as a simple, safe, predictable procedure to adjust the refractive outcome after the initial RK has been performed. Most ideas to contend with the corneal shape after this event have been purely empirical. Thus an easy method to fine-tune a refractive correction that is minimally invasive and easily performed, would require serious consideration.

Laser stromal ablation procedures, such as photorefractive keratectomy (PRK) for correction of refractive disorders are currently popular and have had reasonable success. These procedures are not, however, spared from the problem of unpredictability. Essentially, in the treatment of myopia, laser energy is imparted to the central cornea thereby causing excision of more tissue centrally and a resultant flattening of the cornea. Unfortunately, the final refractive effect is determined not only by the amount of ablation but also by the healing response to the keratectomy. The cornea actively lays down new collagen and the epithelium undergoes a hyperplastic response, among other responses, in an attempt to repair the damage to its surface. This causes regression, or a shift backwards towards myopia, which can gradually occur over a period of months to years. An undesired effect of new collagen deposition is stromal scar formation which manifests as stromal haze and possible decrease in contrast sensitivity by the patient. This corneal stromal opacification is variously referred to as fibrosis, scarring, or haze which is associated with reduced visual acuity and contrast sensitivity, regression of the refractive effect, and poor night vision. Predictability with PRK is an issue, as with RK. Most published results of outcome after PRK treatment for myopia show 80–94% of eyes obtaining uncorrected visual acuity of 20/40 or better while the percentage of patients achieving 20/20 is significantly less. These numbers are in spite of the fact that there is a range of residual refraction at which the patient can still see 20/20 as previously explained. It can be assumed that a significant proportion of those achieving 20/20 after PRK are actually slightly hyperopic. It may very well be that with time, a significant percentage of those patients develop "progressive hyperopia", or an unmasking of the latent hyperopia. So, although the percentage of patients achieving 20/20 after PRK is not acceptable by the definition of an ideal refractive procedure, it may be inflated as was the initial results with RK. Although visual recovery is slow in RK, it is quicker than after PRK. A second laser ablation procedure is usually undertaken with caution since it may cause a greater healing response with even more regression than the initial procedure. Again, as in RK, the laser ablation procedure is not completely predictable, partly because one cannot predict an individual's wound healing response.

For years it has been thought that refractive surgery with intracorneal implants could be used in the correction of ametropia. Early techniques included lamellar removal or addition of natural corneal stromal tissue, as in keratomileusis and keratophakia. These required the use of a microkeratome to remove a portion of the cornea followed by lathing of either the patient's (keratomileusis) or donor's (keratophakia) removed cornea. The equipment is complex, the surgical techniques difficult, and most disappointingly, the results quite variable. The current trend in keratorefractive surgery has been toward techniques that are less traumatic to the cornea, that minimally stimulate the wound healing response, and behave in a more predictable fashion. The use of alloplastic intracorneal lenses to correct the refractive state of the eye, first proposed in 1949 by Jose Barraquer, have been plagued with problems of biocompatibility, permeability to nutrients and oxygen, corneal and lens hydration status, etc. Other problems with these lenses included surgical manipulation of the central visual axis with the concomitant possibility of interface scarring.

More recent efforts toward the correction of refractive errors have focused on minimizing the effects of the wound healing response by avoiding the central cornea. There have been multiple attempts to alter the central corneal curvature by surgically manipulating the peripheral cornea. These techniques are discussed because of their specific relevance to this invention.

Zhivotosvskii, D. S., USSR patent no. 3887846, describes an alloplastic, flat, geometrically regular, annular ring for intracorneal implantation of an inside diameter that does not exceed the diameter of the pupil. Refractive correction is accomplished primarily by making the radius of curvature of the surface of the ring larger than the radius of curvature of the surface of a recipient's cornea in order to achieve flattening of the central area of the cornea. Surgical procedures for inserting the ring are not described.

A. B. Reynolds (U.S. Pat. No. 4,452,235) describes and claims a keratorefractive technique involving a method and apparatus for changing the shape of the optical zone of the cornea to correct refractive error. His method comprises inserting one end of a split ring shaped dissecting member into the stroma of the cornea, moving the member in an arcuate path around the cornea, releasably attaching one end of a split ring shaped adjusting member to one end of the dissecting member, reversibly moving the dissecting member about the path, and thereby pulling the adjusting member about the circular path, made by the dissecting member, withdrawing the dissecting member, adjusting the ends of the split ring shaped adjusting member relative to one another to thereby adjust the ring diameter to change the diameter and shape of the cornea and fixedly attaching the ring's ends by gluing to maintain the desired topographical shape of the cornea.

A major advantage of this ring was that a very minimal wound healing effect was expected. A marked corneal wound healing response would decrease the long-term stability of any surgical refractive procedure. However, there are two distinct problem areas affecting the refractive outcome of surgical procedures treating ametropia:

1. The first problem is concerned with the ability to predetermine the shape and size of a implant that will lead to a certain refractive outcome. In RK or PRK, retrospective studies have been performed that led to the development of nomograms which predict that a certain depth cut or a certain ablation amount will result in a predictable amount of correction. In the case of the ring, eventually nomograms will be developed that can be used to predict a given refractive correction for a given thickness or size of the ring. However, these nomograms can never fully account for individual variability in the response to a given keratorefractive procedure.
2. The refractive outcome also depends on the stability of the refractive correction achieved after surgery. To reiterate, the advantage of the ring would be the stability of the refractive outcome achieved because of a presumed minimal wound healing response. This decreases the variability of the long-term refractive outcome but still does not address the problems posed in the first problem area,—the inherent individual variability, in that while the outcome may be stable, it may very well be an inadequate refractive outcome that is stable.

Another unaddressed issue is that even with the implant, surgeons will aim for a slight under-correction of myopia because, in general, patients are more unhappy with an over-correction that results in hyperopia. Again, the refractive outcome may be more stable than in RK or PRK but it may be an insufficient refractive result that is stable.

Simon (U.S. Pat. No. 5,090,955) describes a surgical technique that allows for modification of the corneal curvature by inter-lamellar injection of a synthetic gel at the corneal periphery while sparing the optical zone and intra-operative removal of such gel to decrease the volume displaced and thus adjust the final curvature of the central corneal region.

Siepser (U.S. Pat. No. 4,976,719) describes another ring-type device to either flatten or steepen the curvature of the cornea by using a retainer ring composed of a single surgical wire creating a ring of forces which are selectively adjustable to thereby permit selective change of the curvature of the cornea, the adjustable means comprising a turnbuckle attached to the wire There are several mechanisms by which peripheral manipulation of the cornea affects anterior corneal curvature. The cornea, like most soft tissues, is nonlinear, viscoelastic, nonhomogeneous, and can exhibit large strains under physiologic conditions. The whole eye is geometrically extremely complex and the biomechanics technique capable of systematically modeling this reality is the finite element method which assumes small strains (a measure of deformity), homogeneity, and linear elastic behavior. Two simple mechanisms will be briefly described.

A simple example is helpful in understanding the first mechanism. Assume a loose rope R between two fixed points P1 and P2 as in FIG. 4a, which forms a curve, the lowest point P being in the middle. Referring to FIG. 4b, a weight w placed on the rope between the middle point P and one fixed point will cause the central portion of the rope to straighten. The cornea C demonstrated in FIG. 5(a) and FIG. 5(b) behaves similarly, the two fixed points, P1 and P2, analogous to the limbus of the eye and the weight W similar to the intrastromal implant 30 which, when inserted in the cornea in surrounding relation to the corneal central optical zone, causes the corneal collagen fibers to deviate upwards at (21) above the implant, and downwards at (22) below the implant. In essence, this deviation of the cornea around the peripheral implant caused by volume displacement in the peripheral cornea results in other areas of the cornea losing "slack", or relatively straightening as shown at (23).

Mechanical expansion of the implant diameter as shown by expansion of the implant 30 in FIG. 6(b) as compared to FIG. 6(a) also flattens the central corneal curvature whereas constriction of the implant 30 steepens the central corneal curvature, analogous to the two fixed points in the example, FIG. 4(a) and FIG. 4(b), being moved together and causing the rope in the middle to sag more. This is permitted to occur, in part, because the boundary nodes at the limbus are not completely fixed. In summary, there is a micro-deviation caused by the bulk of the implant 30 itself within the peripheral tissue, slightly flattening the central curvature of the cornea, and a constricting or expanding implant altering the fixed points and thus altering corneal curvature. A constricting or expanding implant is likely to cause a less stable refractive outcome because the inward or outward forces of the implant against the corneal stroma may gradually cause further lamellar dissection and dissipation of the forces. A more consistent outcome is likely to be achieved with varying the volume displaced in the peripheral cornea as described by Simon.

The second mechanism is aptly described by J. Barraquer in the following quote. Since 1964, "It has been demonstrated that to correct myopia, thickness must be subtracted from the center of the cornea or increased in its periphery, and that to correct hyperopia, thickness must be added to the center of the cornea or subtracted from its periphery." Procedures involving subtraction were called 'keratomileusis' and those involving addition received the name of 'keratophakia'. Intrastromal corneal ring add bulk to the periphery and increasing the thickness of the ring results in a more pronounced effect on flattening of the anterior corneal curvature by "increasing (thickness) in its periphery".

The ideal keratorefractive procedure allows all the advantages of eyeglasses or contact lenses, namely, being able to correct a wide range of refractive errors, accuracy or predictability, allowing reversibility in the event that the refractive state of the eye changes and it becomes necessary to adjust the correction again, yielding minimal complications, and associated with technical simplicity, low cost, and being aesthetically acceptable to the patient. The goal of refractive surgeons should be to achieve 20/20 uncorrected visual acuity with long-term stability in greater than 95% of patients. None of the currently available refractive surgery procedures generate this degree of accuracy or stability.

Once again, an easy procedure to post-operatively fine-tune the refractive correction and corneal curvature which is often influenced by changes in corneal hydration status, wound healing responses, and other unknown factors, is not available. Each of the techniques described suffers from a limited degree of precision. In this disclosure of the present invention, an easy method to adjust the refractive outcome after the corneal curvature has stabilized, a method that is minimally invasive, a method causing minimal stimulation of the wound healing processes, allowing repetitive adjustments as deemed necessary, and being almost completely reversible is described. It may make moot the pervasive issue of unpredictability and make obsolete the application of procedures which rely heavily upon nomograms to predict refractive outcome and are thus unable to adequately account for an individual's variable response to the procedure.

SUMMARY OF THE INVENTION

The present invention concerns the use of an adjustable intrastromal device adapted for implantation in the cornea and formed of a flexible hollow shell composed of a material such as a silicone or urethane polymer, with an annular chamber that may be augmented with a biocompatible filler material such as polymethylmethacrylate (PMMA). The filler material can be any biocompatible material of any shape or length but preferably is ring-shaped and a flexible elongated strand-like filament of a variable size. The device is filled with a predetermined amount of the biocompatible material described, and implanted in the cornea in surrounding relation to the optical zone of the cornea. The corneal curvature is then adjusted by complete removal of one or more rings thus modifying the volume of the device in a discrete fashion and resulting in steepening of the corneal curvature and a myopic shift. This relatively simple adjustment for refractive correction can be performed with surgical instruments commonly available and requires minimal post-operative manipulation of the cornea and the implanted device. The apparatus of the invention is an adjustable implantable device including an outer membrane forming an enclosure for receiving a filler material such as multiple rings and adapted to be inserted into the interlamellar space of the corneal stroma for the purpose of correcting refractive error. The volume displaced by the device is easily modified on multiple occasions following the initial surgery of implantation and thus allows for adjustment of the refractive outcome at a later date without necessitating the removal of the implanted device.

DESCRIPTION OF THE DRAWINGS

FIG. 6(a) and 6(b) are cross sectional schematic views of a cornea for showing the effect produced by an expansion of the adjustable implant of the invention after its implantation in the cornea;

DETAILED DESCRIPTION OF THE INVENTION

Figure 1:
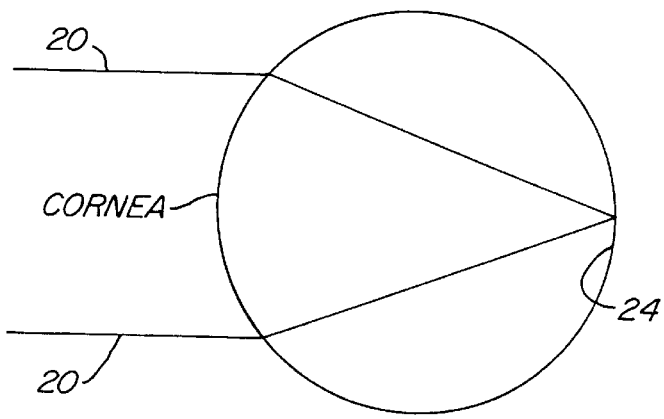
FIG. 1 is a schematic representation of a horizontal section of the human eye.
Figure 2:
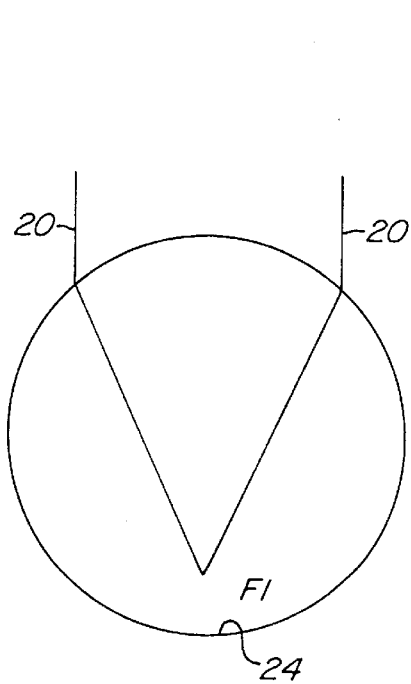
FIG. 2 is a schematic representation showing how the light rays focus in front of the retina of the eye in the condition of myopia.
Figure 3:
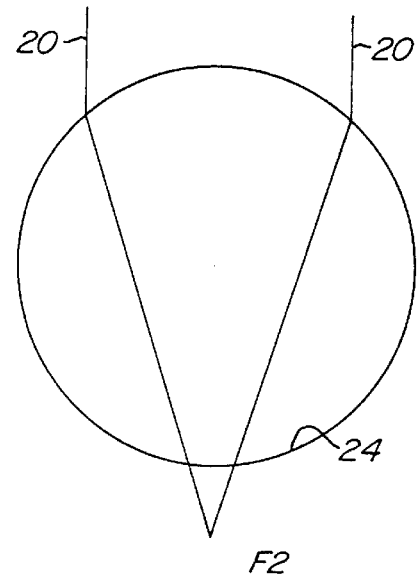
FIG. 3 is a schematic representation showing how light rays focus in front of the retina of the eye in the condition of myopia.
Figure 4A:
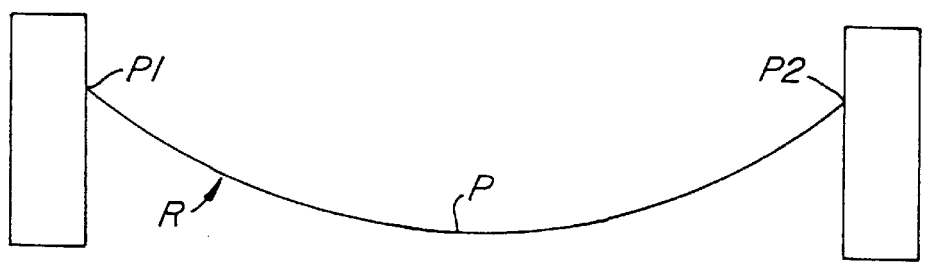
FIG. 4(a) is a schematic illustration for showing a rope suspended at its ends between two fixed points.
Figure 4B:
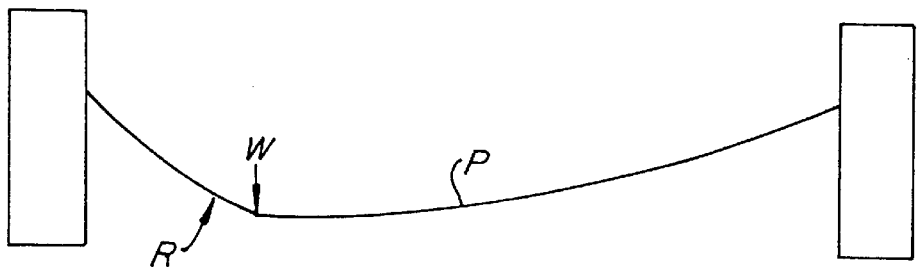
FIG. 4(b) is a schematic illustration which shows the rope in FIG. 4(a) with the force of a weight applied to the rope between its midpoint and one of the fixed points.
Figure 5A:
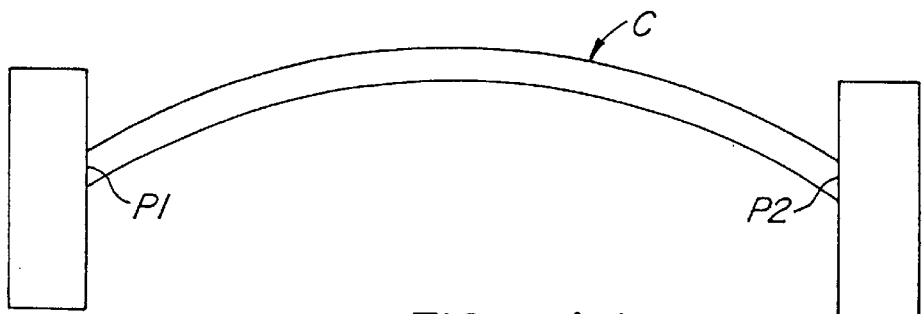
FIG. 5(a) is a schematic illustration showing the cornea of an eye wherein the cornea is fixedly attached at diametrically opposed points on the surrounding limbus.
Figure 5B:
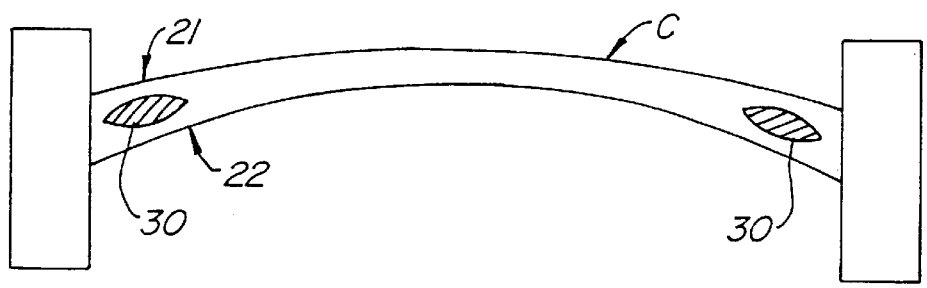
FIG. 5(b) is an illustration similar to FIG. 5(a) but showing the curvature effects produced on the cornea because of the presence of an intrastromal support implant in the cornea.
Figure 7A:
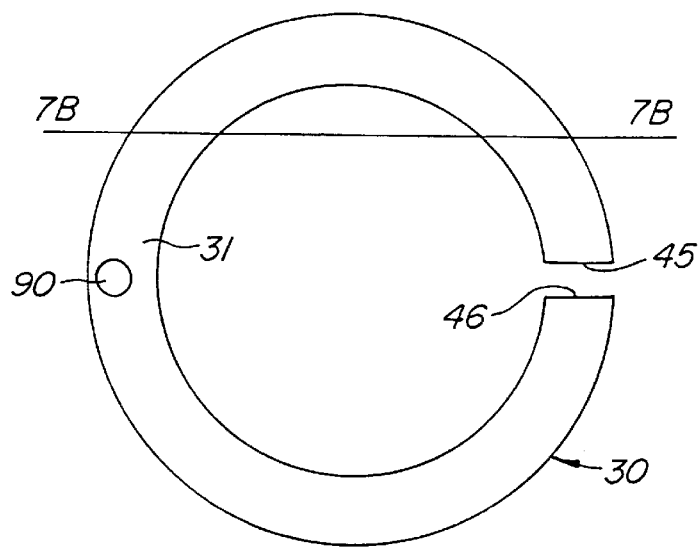
FIG. 7(a) is a plan view of the flexible device of the invention wherein the device has been severed by a radial cut.

Referring more particularly to the drawings, there is shown in FIG. 7(a) the apparatus of the invention which comprises an adjustable device 30. The device 30 forms an enclosure for receiving a filler which is easily removable, such as a PMMA ring or other strand-like materials such as nylon, Nurolon, polypropylene, Mersilene, Dacron, polyimide, or other polymeric materials such as fluoropolymer resins. The device filler material can be any biocompatible material but preferably is a flexible, filamentous structure that may be constructed from a resilient polymeric substance such as that described above. The terms ring and strand are used interchangeably in this document. The cross section of the ring may be of various geometric shapes including circular, oval, rectangular, square, or triangle. The cross-sectional area of the ring can vary in dimension along its length. The device may contain one or more rings, each of which is removable at a later time.

The device 30 comprises a tubular shell 30a made of a flexible material, such as a silicone, acrylic or urethane polymer and in FIG. 7(a) is shown as a split donut shape. The shell material has adequate stiffness such that the device will maintain its generally circular shape in plan view when sufficiently filled and also have adequate flexibility to allow an increase in thickness with filling as shown in the cross section view of FIG. 8(b) and flattening with removal of the ring as shown in FIG. 8(c). The shell of the device must have sufficient structural integrity, strength and flexibility to generally maintain its circular shape and be expandable. Its composition material may be similar to that used in producing foldable or deformable intraocular lenses such as a silicone polymer, urethane polymer or acrylic polymer, or that material used in soft contact lenses or materials such as fluoropolymer resins.

Figure 7B:
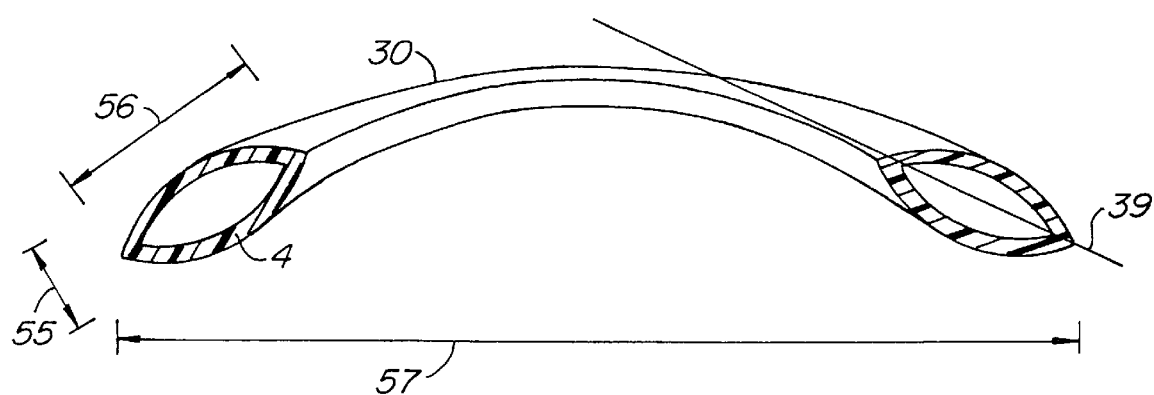
FIG. 7(b) is an enlarged diametral cross section view as taken along the section line 7b—7b in FIG. 7(a)
Figure 8A:
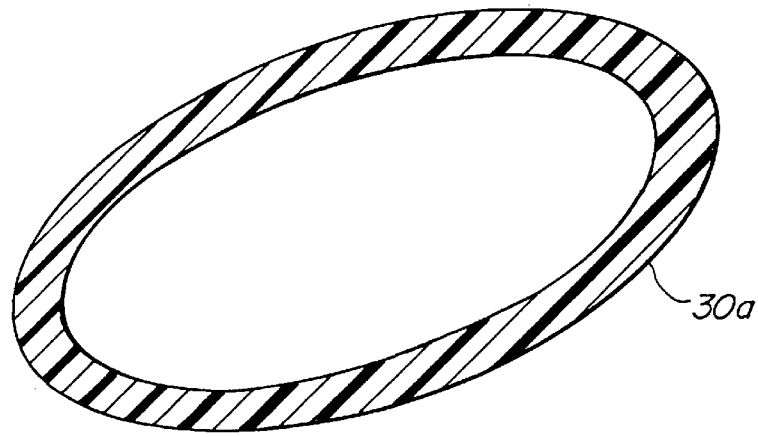
FIG. 8(a) is a cross-section view of a device of the invention.
Figure 8B:
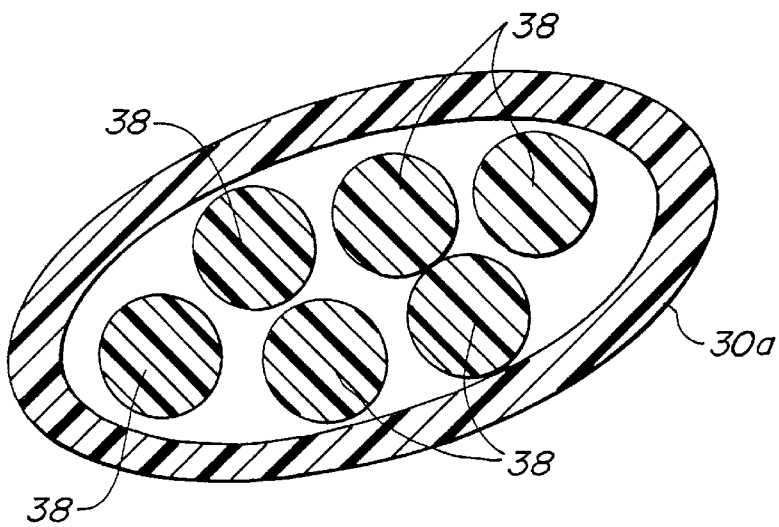
FIG. 8(b) is an enlarged radial cross section view of the tubular device of the invention wherein the interior of the device has been filled with a number of rings.
Figure 8C:
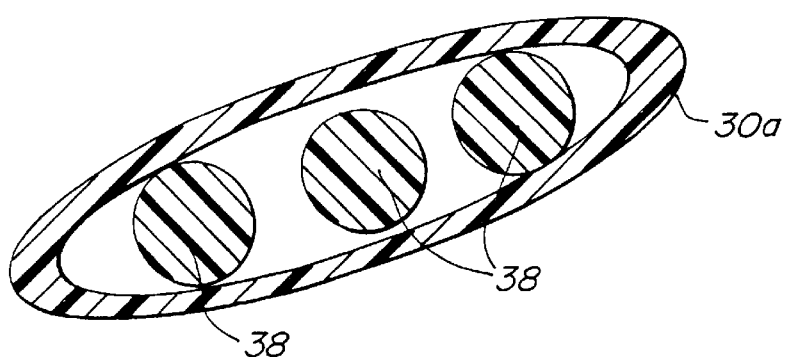
FIG. 8(c) is a cross section similar to FIG. 8(b) but wherein some of the rings shown in FIG. 8(b) have been removed from the device.
Figure 9:
FIG. 9 is a perspective diametral section view of the device of the invention, showing the angle of the conic shaped radial cross sections.

The cross section of the device 30 as taken in a radial plane through the center of the implant is elliptically shaped as seen in the section views demonstrated in FIG. 8(a) and in FIG. 9. The different embodiments shown in FIGS. 10(a)–10(d) can each be modified to provide a number of sub-embodiments by altering variables such as the composition material of the device wall, manner of device connection, type of ring filler material, and cross-sectional surface parameters of the device, e.g., forming the device from cross sections in the form of a circle, square, rectangle, triangle, oval, etc. The major axis 39 of a transverse cross section of the device 30 is such that it corresponds to the slope of the corneal arc of the anterior pole of the cornea, thus forming the conic section. This angle is approximately 25 to 35 degrees as shown in FIG. 7(b). The two ends 45, 46 of the device are squared off so that they may juxtapose each other as shown in FIG. 7(a) and may be fixably joined at the time of surgery by such methods as suturing or gluing.

Figure 10A:
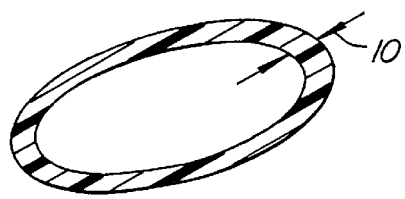
FIGS. 10(a)–10(d) are radial cross section views of modified forms of the device of the invention.
Figure 10B:
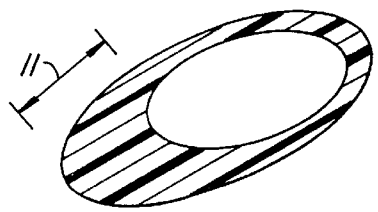
Figure 10C:
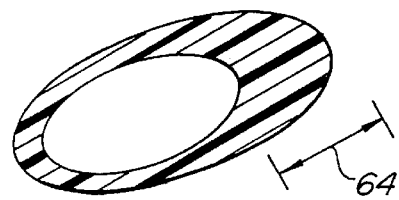
Figure 10D:
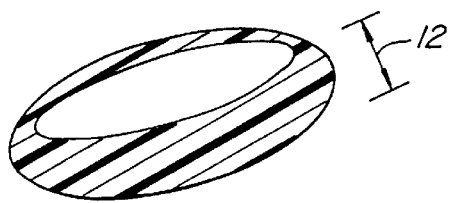
Figure 11:
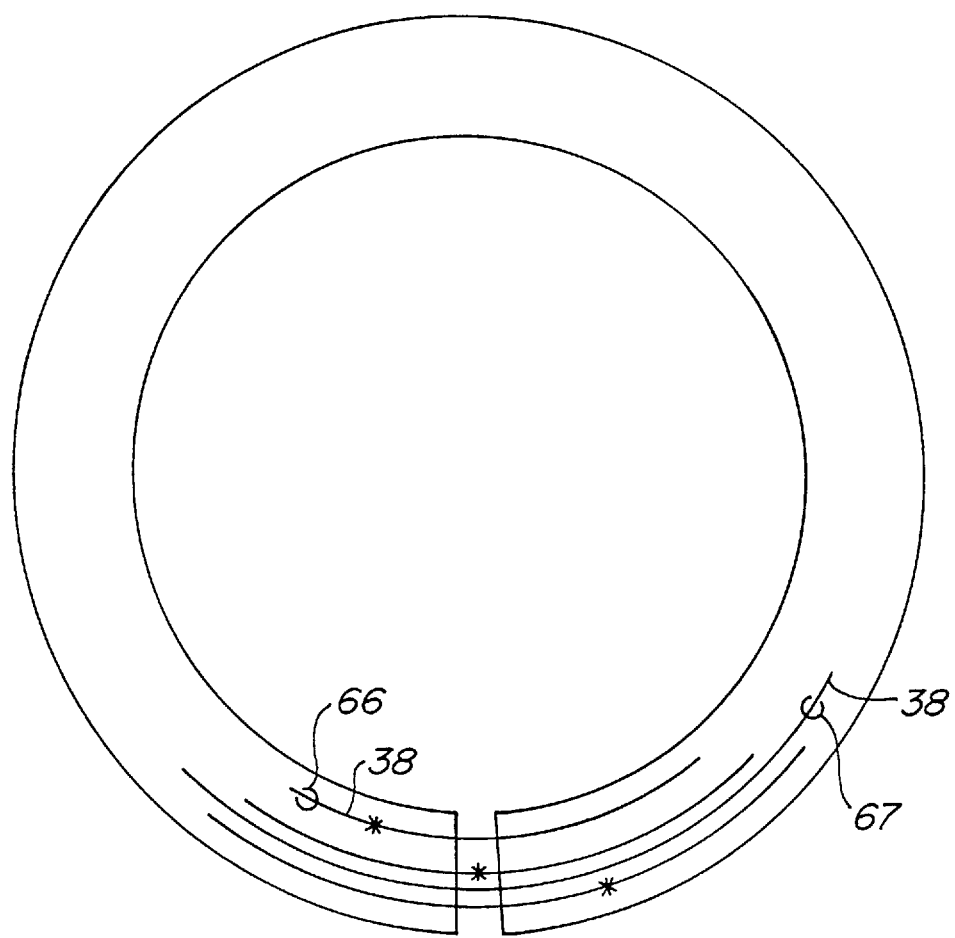
FIG. 11 is a plan view of the device showing possible ring connection placement along the ring placed inside the implant.

The device 30 is adapted to be implanted into the peripheral stromal cornea. It is of a thickness and geometry such that when implanted it alters the central corneal curvature without intruding into the central optical zone of the cornea and without decreasing the diffusion of nutrients to the central cornea. It is of a size such that it can be readily inserted into the peripheral human cornea intrastromally and consists of a flexible material which is biocompatible, and more specifically, compatible with ocular tissues. The dimensions as shown in FIG. 7(b) include a thickness (55) of 0.1–1.5 mm, width (56) of 0.4 to 2.0 mm and an outer over-all diameter (57) of 6.00 to 11.0 mm. The thickness of the shell 30(a) of this device 30 may be varied as shown in FIGS. 10(a)–10(d). The device may contain only one or multiple rings 38 of varying diameter and composition. The ring 38 may be composed of a permanent biocompatible material as used in ophthalmic surgery such as polymethylmethacrylate, nylon, mersilene, prolene, or polypropylene and can vary from 0.02 mm in diameter to 1.0 mm in diameter. The ring may be clear or colored. The ring may be marked towards the head and tail end of the device to aid the surgeon in adjusting the tension when connecting the ends of a ring. The ring may have a pre-fabricated loop 66, 67 at one end as shown in FIG. 11 which would facilitate removal of the ring by using an instrument having a small hook at the operative end with which the loop can be snared. Instead of a loop, the ring end may have some other configuration such as a rounded or thickened end which would also facilitate grasping the ring. The loop also aids in preventing surrounding rings from being pulled out simultaneously by providing resistance at the open end. The two ends of the ring are not necessarily connected.

The device of the invention is designed to be implanted in the cornea of the eye to alter the external curvature of the central optic zone of the cornea without encroachment into the optic zone. It is comprised of a hollow device with a variable internal volume such that the central optic zone is flattened by disconnecting a ring that has been connected with tension, or steepened in curvature by ring removal to an amount suitable to provide the refractive correction needed and allowing for adjustment of over-correction or under-correction of the refractive error.

Depending on the amount of refractive error, an appropriate embodiment varied in shape, size, circumference, ring size, ring composition and number of ring, are chosen. The flexible shell 30a containing the ring material can also be varied as shown by the embodiments of implant illustrated in FIGS. 10(a)–10(d). The choices include:

1. The absence of a supporting polymethylmethacrylate (PMMA) backbone.
2. PMMA or other stiff physiologically acceptable polymer backbone reinforcing the inner circumference of the device wall as shown in FIG. 10(c). The thickened areas 64 shown in FIG. 10(c) may be increased thickness of the flexible material composing the walls or it may be the stiff polymer backbone mentioned above. During surgery, the inner circumference backbone could be appropriately adjusted and fixed with suture or glue, with gross adjustments aided by the use of a keratometer.
3. PMMA or other stiff polymer backbone reinforcing the outer circumference of the device wall as shown in FIG. 10(b).
4. Support of both inner and outer circumferences.

The size of the device chosen should be such that the range of over-correction or under-correction secondary to individual variability of response to surgery may be comfortably corrected (not requiring removal of all of the ring) by the methods described. The maximal thickness, circumference, and type of supporting backbone is chosen prior to insertion of the implant. The ideal embodiment, given the preoperative refractive state and other pertinent data, is chosen prior to operating and then that embodiment further manipulated as necessary to determine the ideal curvature. The device is inserted into the peripheral cornea at an adequate depth and then further adjusted in order to more precisely adjust the shape of the cornea and focus the light entering the eye on the retina. The intra-operative keratoscope or automatic keratometer may be helpful. However, intra-operative curvature measurements in surgeries involving the cornea have not been shown to be predictably reproducible.

The device is implanted into a circular lamellar channel formed at ½ to ⅔ corneal depth with a circular dissecting instrument that requires only a small midperipheral corneal incision. A knife is used to make an approximately 2 mm radial incision beginning at 2.5 to 3.5 mm from the corneal center. The surface of the cornea is cut only at this incision. A Suarez spreader is introduced into the bottom of the incision and a small lamellar channel created. Application of a vacuum centering guide is used to fix the globe while an 8–9 mm outer diameter lamellar channeling tool introduced through the incision into the lamellar channel is rotated to produce a 360 degree channel around the corneal midperiphery at ½ to ⅔ corneal depth. After the channeling tool is removed, a circular endoscopic-type forceps is inserted into the same channel and rotated 360 degrees such that the forcep tip emerges from the radial incision. One end of the device is inserted into the forceps, the forcep jaws closed thus gripping the device, the circular forceps rotated until the device is progressively pulled into place. The head and tail of the device are brought together and may be fixed together with suture or glue.

In summary, adjustment or choice of device size, shape, width, shell thickness, and circumference, factors affecting the corneal curvature and refractive outcome, occurs in three distinct temporal stages:

1. Preoperatively, the above mentioned variables and presence or absence of a supporting backbone are chosen using nomograms developed from retrospective studies as a guide to the selection of each variable.
2. Intra-operatively, the device tightness is adjusted as necessary, aided by the use of the intra-operative keratoscope if necessary. The ring passing completely around the implant may be tightened and connected at various tensions, keeping the following in mind:
   a. Adjusting the volume of the implant probably results in a more predictable change in corneal curvature than attempting to adjust corneal curvature by either the application of tension or the removal of tension.
   b. If a hyperopic correction is required, circular radial forces will be necessary to maintain the corneal curvature and either the head and tail of the device connected at tension or one or more rings connected at tension.
3. Post-operative adjustments. Simple, easily performed postoperative adjustments, which avoid the complications of re-operation concomitant with most keratorefractive procedures, are rendered feasible by this mechanism of adjustment. This postoperative adjustment can compensate for an inadequate preoperative implant choice, for corneal hydration intra-operatively which results in a different corneal curvature after corneal hydration status changes post-operatively, for an unexpected wound healing response in the periphery to the implant, and for later refractive changes caused by unknown factors. This postoperative adjustment is made possible by a flexible corneal device containing several rings which can easily be removed thus modifying the volume of the device and resulting in increased corneal curvature.

Figure 12A:
FIGS. 12(a) and 12(b) show cross-sectional views of the cornea and device before and after connected ring placed inside the implant are cut.
Figure 12B:
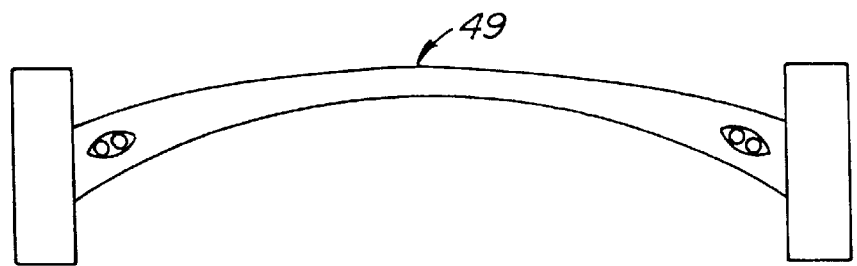
Figure 13A:
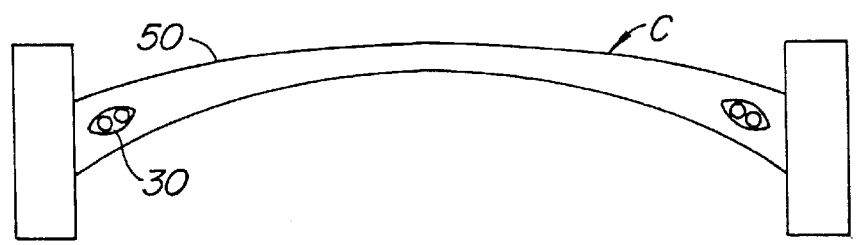
FIGS. 13(a) and 13(b) show cross-sectional views of the cornea and implant before and after a ring is removed therefrom.
Figure 13B:
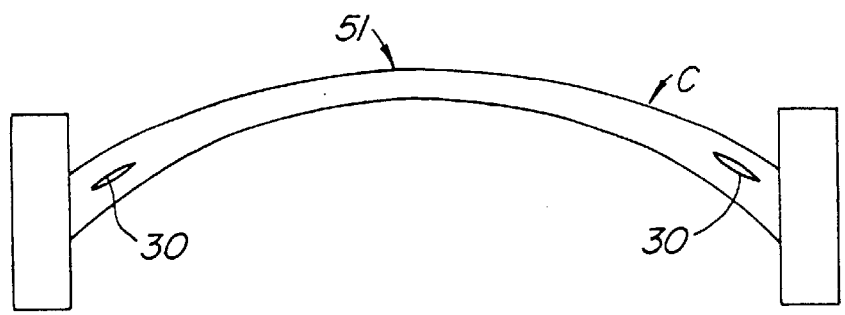

The cornea is cut at any point anterior to the ring, preferably over the area where the shell has a portion of the anterior shell removed, thus providing easier access to the ring. The strands may also be removed from the initial incision site. When the rings are removed from a site other than the head or tail of the device, the head and tail may be closed such that strand removal results in a partial vacuum formation which facilitates ring collapse. Ring removal from the device minimally disturbs the stromal-implant interface compared to removing the device itself, thus minimizing the effects wound healing and edema will have on the adjustment. This postoperative adjustment appears to be a necessary adjunct to any method that seeks to meet the criteria for the ideal kerato-refractive procedure. If the refractive outcome is not ideal, these are the steps that may be taken:

a. As demonstrated in FIGS. 12(a) and 12(b), if the corneal curvature is too steep and the patient is myopic, and if there is a ring connected at tension (38) it may be cut thus releasing some of the constricting circle of forces and thus flattening the corneal curvature (49). Ideally, the ring is cut near the initial incision site. The ring may be cut with a sharp needle, knife, or even with a laser. If still inadequate, more than one ring may be cut. The two ends of the device are unlikely to drift even if all the rings are cut. In the case that ring cutting results in excessive flattening, one of the rings may be completely removed from the device and eye, resulting in a relative decrease in volume of the device with a concomitant steepening of the corneal curvature. If, in the unlikely event that a ring is difficult to remove, that ring may be cut at 180 degrees away and then each half removed through the initial incision. Corneal curvature may be decreased by another method. A ring or other solid biocompatible material within the device may be attached to a larger diameter ring such that as the ring within the device is removed, the larger ring is progressively pulled into place thus increasing the volume of the device and flattening the anterior corneal curvature.

b. As shown in FIGS. 13(a) and 13(b), if the corneal curvature 50 is too flat after surgery (FIG. 13a), rings that have relatively little or no tension may be cut and removed, thus steepening the corneal curvature as shown in FIG. 13(b) with a myopic shift as described above. This is why some of the rings are connected with little or no tension at the initial surgery. If there is over-correction of the adjustment and removal of the ring results in excessive steepening, a ring with tension may be cut and left in place, thus flattening the cornea or a larger new ring may be pulled into place.

Figure 14A:
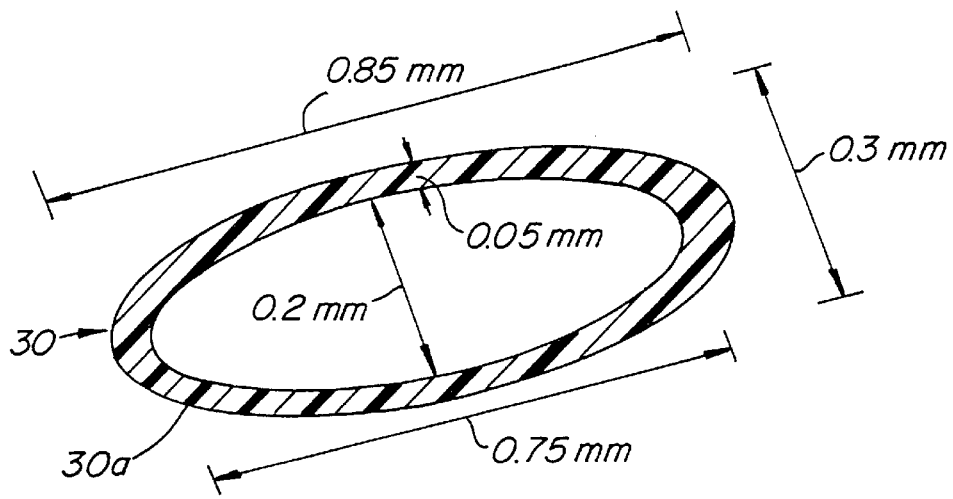
FIG. 14(a) is a radial cross-section of the device of the invention and showing typical dimensions thereof.
Figure 14B:
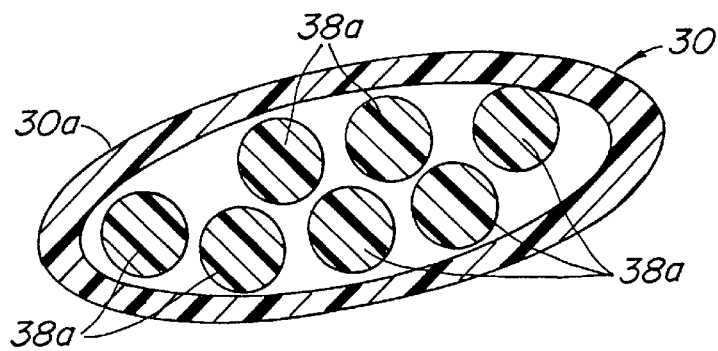
FIG. 14(b) is an enlarged radial cross section of the device in FIG. 14(a) wherein the interior of the device is filled with several rings.
Figure 14C:
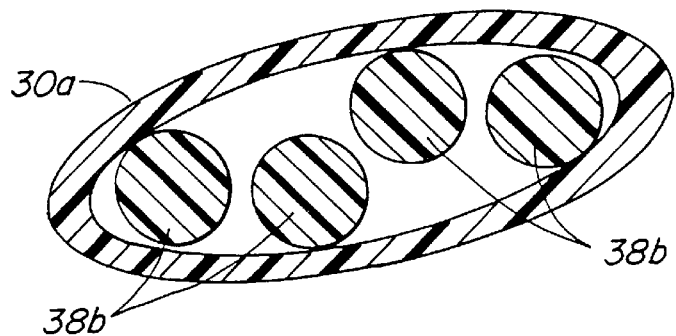
FIG. 14(c) is an enlarged radial cross section similar to FIG. 14(a) but showing the device interior filled with a lesser number of rings which are of greater diametrical thickness.

A typical adjustable device 30 of the invention is shown in FIG. 14(a). The width of its outer diameter is 0.85 mm, overall thickness is 0.3 mm, and larger inner diameter is 0.75 mm and minor diameter is 0.20 mm. A device of this size is expected to correct myopia by approximately 3 diopters. To calculate the number of rings which will comfortably fit and the diopter change with removal of each ring, the following is assumed. The cross-sectional area of the oval-shaped device is approximately 0.11 mm squared. Since this volume cannot be completely filled with rings that have round cross-sections—there are spaces between the round rings, the area that will be occupied by a ring is 78.5% ideally. Approximately four (0.175 mm diameter) rings 38b or seven (0.125 mm diameter) rings 38a will fit into this space. Complete removal of all rings results in flattening by 0.2 mm or a 2.0 Diopter change. The average diopter change for each 0.175 mm diameter ring removed from this typical embodiment is 0.5 diopter, for each 0.125 mm diameter ring removed, 0.3 diopter change. Given an initial myopic patient, the outcome can be overshot by 50% of the initial refraction and the hyperopia still reasonably managed by ring removal alone. Over-treatment resulting in hyperopia is a significant disadvantage in most kerato-refractive procedures. In radial keratotomy the wound healing processes occur over a period of years and there is often a progressive hyperopia. Patients who become symptomatically hyperopic after surgery are extremely unhappy. Therefore most surgeons use nomograms that attempt to achieve a slight under-correction. Concerning photorefractive keratectomy, in one study, it was found the main reason patients did not have their second eye corrected with PRK (given that their first eye was corrected with PRK) was because of dissatisfaction with the hyperopia in their operated eye. The technique described herein easily corrects over-correction hyperopia.

Figure 15A:
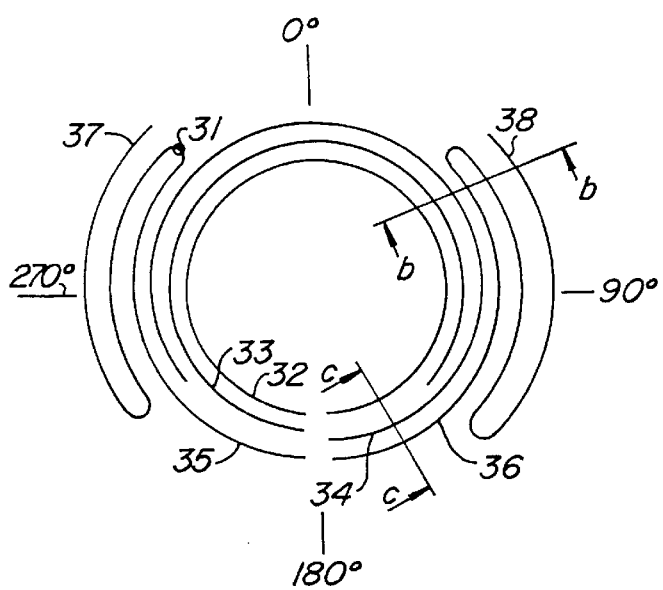
FIG. 15(a) is a schematic plan view of the orientation and form of a plurality ring material which may be inserted into the interior of the device; the spacing therebetween exaggerated for purpose of illustration.
Figure 15B:
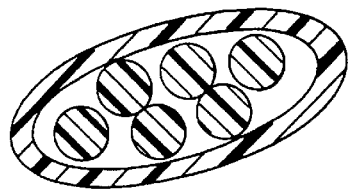
FIGS. 15(b) and 15(c) are cross sections of the device of the invention as taken along the section lines b—b and c—c in FIG. 15(a), respectively.
Figure 15C:
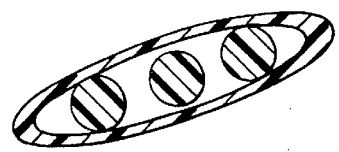
Figure 16A:
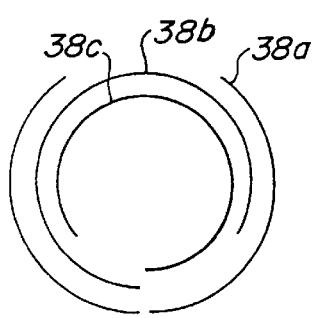
FIGS. 16(a), 16(b), and 16(c) show variations in the configuration and orientation of rings which are suitable for insertion in the device.
Figure 16B:
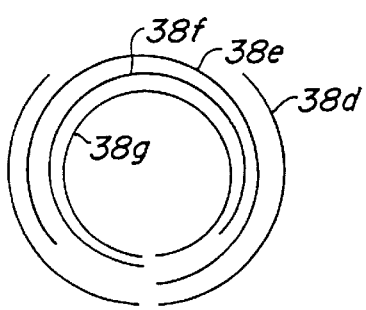
Figure 16C:
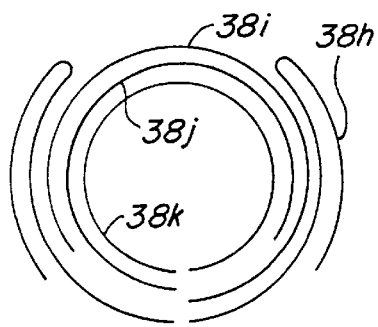

In a simple adaptation of the this technique, this device may be used to correct astigmatism. Curvature variation of the anterior surface of the cornea is responsible for the majority of cases of astigmatism. The light rays converge upon more than one plane and no one principal focus is formed. Astigmatism ordinarily depends on the presence of toroidal instead of spherical curvatures of the refractory surfaces of the eye. To correct astigmatism, certain areas of the cornea must necessarily be corrected to a greater degree than other areas. The implant can be varied in thickness along the circumference of the device with the sections of the device having increased volume corresponding to the areas of the cornea having a steeper slope and requiring greater correction. In the illustration of FIG. 15(a), the ring 32 completes almost 360 degrees within the device. Another partial ring (33) is shorter and is absent at approximately 4–6 o'clock in the drawing. The ring (34) is the mirror image placement of (33), and is absent at 6–8 O'clock. Ring (35) folds over itself twice in the area of increased thickness. Ring (36) is the mirror image placement of (35). The end of the ring (37) is attached to the device by glue or other means. The end of the ring on the other side (38) is likewise fixed. As illustrated by the greater volume of the cross section of the implant in FIG. 15(b) as compared to the size of the cross section in FIG. 15(c), the areas with more ring have augmented volume by up to 50% and thus allow for the differential correction required in astigmatic conditions. If the astigmatism is over corrected, ring (35) and (36) may be pulled until the loop (31) is removed and then cut at the point where the ring emerges from the device. The removal of the loop (31) reduces the ratio of the larger area to smaller area of the implant from 6/3 to 4/3. In the event that the astigmatism is under-corrected, ring (32) may be completely removed, increasing the ratio from 6/3 to 5/2. Many different variations on this theme are possible, with some examples shown in FIGS. 16(a), 16(b) and 16(c). The ring 38a–38c as shown in FIG. 16(a), 38(d)–38(g) in FIG. 16(b), and 38(h)–38(k) in FIG. 16(c) can be varied by the number, length, diameter, presence of one or more loops at the end of a ring, and whether or not the ring is fixed to the device. The variations can occur in the flexible device which may have a supporting backbone of PMMA or other polymeric material. The thickness of the device shell may also be varied. The head and tail of the implant are brought into place and fixed. Ring adjustment is based on principles previously discussed. The manipulation of ring is usually through the initial insertion site, however, the device may have a small circle removed from the anterior shell, to provide a small hole 90 as seen in FIG. 7(a) and located 180 degrees away from the original incision site, through which the ring may be adjusted or removed. The rings are not necessarily 360 degrees in length as seen in FIGS. 15 and 16 and they may also be cut at their mid-length so as to facilitate their removal at a later date.

Figure 17A:
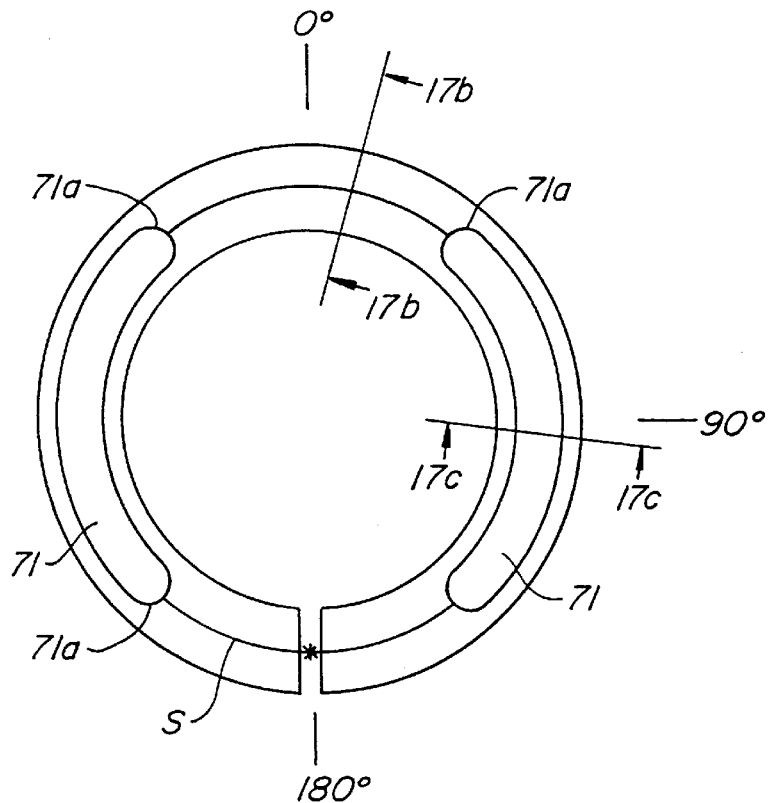
FIG. 17(a) is a schematic showing a plan view of the device of the invention wherein a partial ring has been inserted in the device.
Figure 17B:
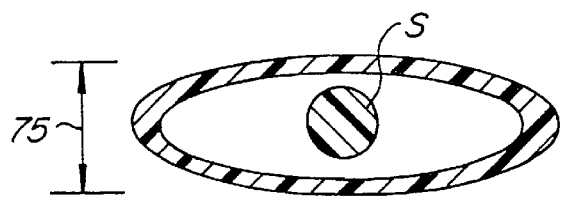
FIG. 17(b) is a view in radial cross section of the device in FIG. 17(a) as taken along the section line 17b—17b.
Figure 17C:
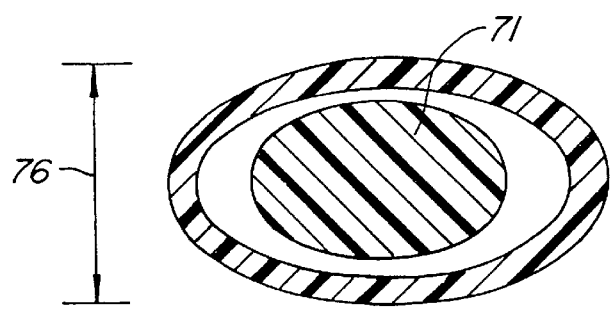
FIG. 17(c) is a view in radial cross section of the device in FIG. 17(a) as taken along the section line 17c—17c.

In another embodiment, the device may have areas of increased thickness formed by the presence of a thicker partial ring 71 that is inserted into the hollow implant shell 30(a) and that may be composed of the same material as the implant wall or a stiffer substance such as PMMA (refer to FIG. 17). This thicker ring 71 may have various transverse cross-section shapes, preferably conforming to that of the device cross-section and more than one thick partial ring 71 may be provided. It may be 10 to 360 degrees in chord length. The ends 71a of the partial rings are gradually tapered so that the thickness at the ring ends approximates the thinnest areas of the device. The thickness of the partial ring can be varied so that the thick section 75 of the device may be several times the thickness of the thinnest sections 76 of the device. 120 to 180 degrees away at the opposite side of the device, there is a similar thick partial ring 71 that may be similar in length and thickness, but not necessarily so. The two partial rings are connected to each other by a strand S as demonstrated in FIG. 17(a). The axis of astigmatism may be adjusted at a later date through the initial incision site by pulling the ring in one direction or the other, thus changing the position of the partial ring within the device chamber and with respect to their direction from the central axis of the device. An individual partial ring may have a ring that connects one end to the other such that each partial ring can be adjusted independently. As previously stated, many different variations on this theme are possible. This particular sub-embodiment may be used with any of the previous processes described. An important advantage of this design is the ease of reversibility of the procedure. The procedure may be completely reversed by the surgical removal of the device or the refractive effect may be partially altered as previously described. The adjustments themselves may be reversed.

Figure 18A:
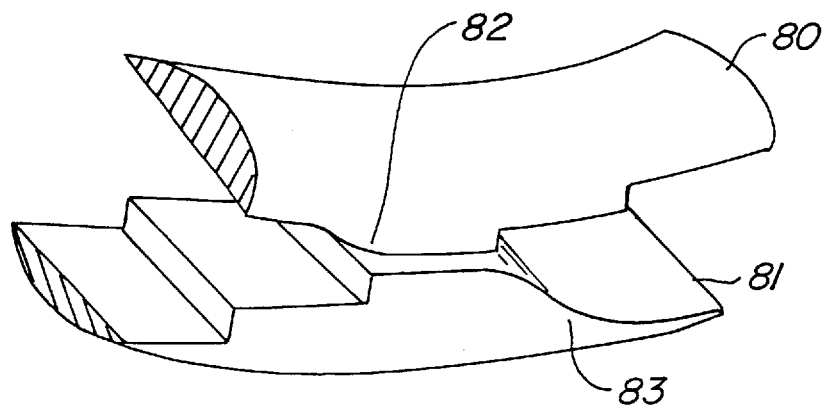
FIG. 18(a) 18(b) and 18(c) are perspective views of an embodiment of an adjustable split-ring strand in three different positions.
Figure 18B:
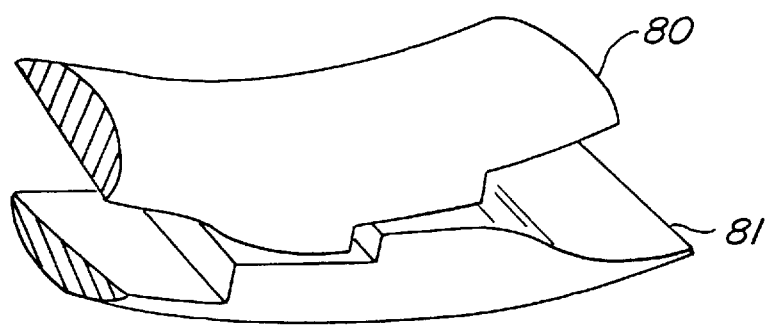
Figure 18C:
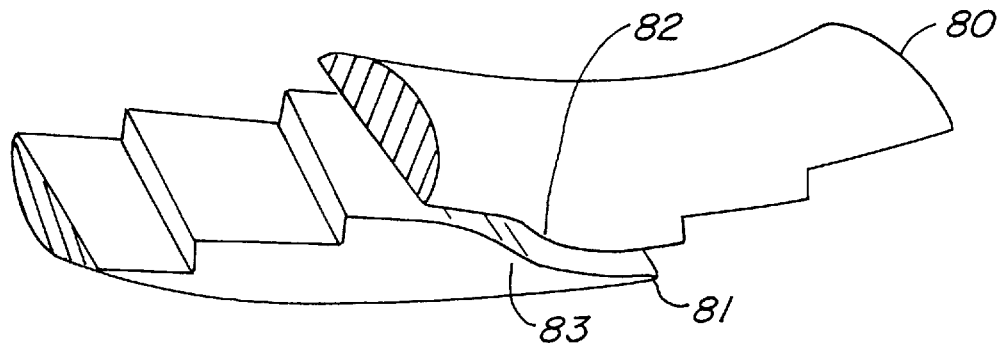

In another preferred embodiment, the outer shell may contain corneal rings which can be adjusted in thickness. In FIG. 18, perspective views of an embodiment with steps are provided. In FIG. 18(a), the highest steps of the upper ring 80 and the lower ring 81 are in contact with each other so that the ring has maximal thickness. In FIG. 18(b), the upper ring 80 is rotated to the left relative to the lower ring 81 such that there is an incremental decrease in the thickness of the ring. The upper ring may be advanced to the left one more step to provide minimal overall ring thickness. At the point of minimal thickness, the upper ring may continue to be rotated to the left as shown in FIG. 18(c) such that the slope of the upper ring 82 rides up on the slope of the lower ring 83 and allows the upper ring to re-establish the position shown in FIG. 18(a). This pattern of steps repeats itself along both the upper and lower rings. This design allows relative stability at each position and yet allows the overall ring thickness to be increased or decreased with relative ease. Ring thickness is adjusted by moving circularly one body member in a direction opposite to the second body member such that the thickness dimension is changed. This may allow adjustment of the thickness prior to surgery or at the time of surgery, but a circular or rotational movement of the rings at a later date will cause shearing of the established corneal-ring interface and additional shearing of the peripheral channel corneal lamellae with an unpredictable effect on anterior corneal curvature. The outer elastic shell permits the interface between the corneal tissue and the device to be relatively undisturbed while allowing the volume of the device to be modified by removing biocompatible material, adjusting rings within the device, or advancing new strands into place.

In yet another useful embodiment, the outer shell of the implantable device is composed of a biocompatible, porous polymer material such as a microporous polypropylene tube or such as that material used in dialysis tubing and membrane filters. The characteristics of the porous shell are similar to that already described including sufficient flexibility to allow the thickness of the device to decrease when the biocompatible filler material is removed. Advantages of a porous shell include improved nutrient diffusion to the anterior corneal stroma.

Another method to allow improved nutrient diffusion to the anterior corneal stroma is to place openings in the shell of the implant. The openings may be multiple, radially or longitudinally oriented, of variable length and width and situated on the anterior or posterior surface of the device.

It is therefore to be appreciated that by use of the present invention, the disadvantages of traditional refractive surgery procedures are avoided, such as 1) progressive hyperopia with radial keratotomy. Hyperopia in any refractive procedure is a generally worse outcome because the patient does not have clear vision at any range and because hyperopia is much more difficult to correct. The described procedure is particularly well-suited to adjust a hyperopic refractive outcome; 2) irreversibility of radial keratotomy and laser ablation surgeries; 3) surgical manipulation of the central visual axis with the potential for scar and stromal haze formation following laser ablation procedures; 4) the need for chronic use of steroid drops with its accompanying complications such as cataract and glaucoma; 5) regression with laser ablation procedures, especially following re-operation; 6) reduction of positive sphericity with RK and laser ablation which may result in increased image aberration; 7) the invasiveness of laser in-situ keratomileusis; 8) lack of precision and predictability with all current procedures; 9) the possible need for repetitive explanting and implanting of ICR'S, which may cause shearing of corneal peripheral channel lamellae with associated decrease in effect and also scar formation.

The last point requires further elaboration. Methods to adjust ring thickness have been described in the prior art. These methods are only discussed in relation to adjusting the ring thickness during implantation, not post-operatively. Attempts to adjust the thickness of the ring are most useful after corneal curvature has essentially stabilized. Adjustments of devices that have been described in the prior art would necessarily require rotation of the ring with resultant shearing of the corneal-ring interface. Rotation of the ring would be required to allow more or less overlap of the individual ring parts thus increasing or decreasing ring thickness. This shearing of the corneal tissue in the immediate vicinity of the ring may alter the corneal curvature in an unpredictable fashion and probably also cause more scarring with possible unpredictable long-term effects. In the embodiment that is described in this article, the device volume is adjusted with only very minimal disturbance of the surrounding tissue. By the nature of the adjustment, there is no rotational movement of the aspect of the device which is in contact with the corneal tissue with respect to the cornea. The corneal-device interface is essentially undisturbed. Of course, with a decrease in the volume of the device, there will be a minute shift of surrounding tissue. In conclusion, a slight decrease in device volume by the adjustment described will not only be much easier to perform, but also have a much more predictable effect.

Most refractive surgery procedures use nomograms to calculate the correction required and cannot completely account for an individual's variable response to refractive surgery. Oftentimes, an enhancement procedure with all its unpredictability is relied upon to correct the residual refractive error, with its concomitant increase in complication rate and scar formation. This new espoused device allows for the fact that individual tissue response to the calculated correction may not be completely predictable, and permits easy adjustments at the time of surgery and more importantly, at a later date after corneal hydration and would healing responses have stabilized by simple ring removal from the device or replacement. The nature of these adjustments minimally disturb the implant-corneal interface (unlike the explantation of the ICR) and is thus expected to have a much more predictable effect than even the implantation of the device itself which causes less of a wound healing response than current procedures such as RK and PRK. In addition, when correcting myopia, a hyperopic outcome is very difficult to correct with any of the current kerato-refractive procedures and over-correction of myopia does occur. In this invention, a hyperopic outcome is relatively easily reversed by ring removal from the implanted device. Typically, in most kerato-refractive procedures for myopia, the surgeon aims for a slight under-correction because of the wish to avoid a hyperopic outcome. The ease with which a hyperopic outcome is adjusted with the device of the present invention enables the surgeon to aim for full correction, thereby obtaining the full benefit of the nomogram, and resulting in a higher percentage of patients with the desired refractive outcome even without a modification of the device. The surgeon may even choose to slightly overcorrect followed by a modification.

Individual responses to any kerato-refractive surgical procedures are variable so that even a "perfect" nomogram will not lead to a reliably predictable result in a particular individual. A simple, safe, and effective technique for corneal curvature adjustment is necessary and such a modification should minimally disturb surrounding tissue thus allowing for a predictable effect. It should also be easily accomplished at some post-operative date after implantation of the device and after factors affecting corneal curvature changes have stabilized. The device of the present invention in its various embodiments is able to have its volume modified with ease at the time of implantation but more importantly on multiple occasions thereafter by simple removal of ring material from the implanted device, thus allowing fine-tuning of the refractive outcome.

In conclusion, in correcting refractive errors with this device and technique, the feeling of finality does not set in even with an initial inaccurate correction, with inadequate adjustment, or even when the last ring is removed because the device itself can be easily removed or better yet, left in place while other refractive procedures, such as laser ablation surgery are considered, if that point is ever reached.

It is also to be appreciated that the foregoing description of the invention has been presented for purposes of illustrations and explanation and is not intended to limit the invention to the precise form of apparatus and manner of practice herein. It is to be appreciated therefore, that changes may be made by those skilled in the art without departing from the spirit of the invention.

I claim:

1. A corneal ring comprising:
   a tubular member to be formed into a ring, the tubular member comprising a biocompatible material; and
   a strand in a cavity of the tubular member, the strand extending at least partially along the length of the tubular member.

2. The corneal ring of claim 1 further comprising at least one additional strand.

3. The corneal ring of claim 1 wherein the tubular member comprises a flexible material.

4. The corneal ring of claim 1 wherein the strand comprises a material selected from the group consisting of polymethylmethacrylate, nylon, mersilene, and polypropelene.

5. The corneal ring of claim 1 wherein the tubular member comprises a reinforcing backbone along at least a portion of the length of the tubular member.

6. The corneal ring of claim 1 wherein the tubular member is porous.

7. The corneal ring of claim 1 wherein the tubular member comprises a plurality of apertures for the exchange of fluids between the cavity and an exterior of the tubular member.

8. The corneal ring of claim 1 wherein the tubular member comprises an aperture to provide access to the cavity.

9. The corneal ring of claim 1 wherein the length of the strand is about equal to the length of the tubular member.

10. The corneal ring of claim 1 wherein the strand has at least one thicker portion.

11. The corneal ring of claim 1 wherein the strand is folded in the tubular member.

12. The corneal ring of claim 1 wherein the perimeter of a cross-sectional area of the strand is angular.

13. The corneal ring of claim 1 wherein the perimeter of a cross-sectional area of the strand is curved.

14. The corneal ring of claim 1 wherein the strand comprises a marking on at least one end.

15. The corneal ring of claim 1 wherein the thickness of the strand is adjustable, the strand comprising a pair of complementary split rings.

16. The corneal ring of claim 1 wherein the strand comprises means for grasping the strand.

17. The corneal ring of claim 16 wherein the grasping means comprises a loop at at least one end of the strand.

18. A process for adjusting the corneal curvature of an eye, the process comprising the steps of:
   making a radial incision into the cornea;
   at the incision, forming an annular channel between lamellae of the corneal tissue, said channel extending about an optical zone of the cornea;
   inserting into the incision an end of a tubular corneal ring, the corneal ring including removable solid filler material in an inner cavity; and
   gradually moving the corneal ring about the annular channel until the corneal ring is fully inserted.

19. The process of claim 18 wherein the solid filler material comprises at least one strand of material extending along at least a portion of the corneal ring.

20. The process of claim 19 further comprising the step of adjusting a radial cross-sectional area of the corneal ring.

21. The process of claim 19 further comprising the step of adjusting a thickness of at least a portion of the corneal ring.

22. The process of claim 21 wherein the adjusting step comprises removing at least one of the at least one strand.

23. The process of claim 21 wherein the adjusting step comprises replacing at least one of the at least one strand with a thicker strand.

24. The process of claim 21 wherein the strand has a thicker portion and wherein the adjusting step comprises moving the strand such that the thicker portion is displaced in the corneal ring.

25. The process of claim 21 wherein the thickness of the strand is adjustable, the strand comprising a pair of complementary split rings.

26. The process of claim 21 wherein the adjusting step comprises the steps of:

in at least one of the at least one strand, connecting a first end and a second end of said strand to form a strand ring; and tensioning the strand ring.

27. The process of claim 26 wherein the adjusting step comprises cutting the tensioned strand ring.

28. The process of claim 21 wherein the adjusting step comprises the steps of:

in the tubular member, connecting a first end and a second end of said tubular member to form a tubular ring; and tensioning the tubular ring.

29. A process of adjusting the corneal curvature of an eye, the process comprising the steps of:

in a first operation making a radial incision into the cornea;

at the incision, forming an annular channel between lamellae of the cornea, said channel extending about an optical zone of the cornea;

inserting into the incision an end of a tubular corneal ring, the ring including at least one strand of solid material in an inner tubular cavity;

gradually moving the corneal ring about the annular channel until the ring is fully inserted; and in a second operation adjusting the thickness of the ring by moving at least one of the strands.

30. The process of step 29 further comprising the step of adjusting a thickness of at least a portion of the corneal ring in the first operation.

31. The process of step 30 wherein the adjusting step comprises removing at least one of said strands.

32. The process of claim 30 wherein the adjusting step comprises replacing one of said strands with a thicker strand.

* * * * *